US012711570B2

(12) United States Patent
Gong et al.

(10) Patent No.: US 12,711,570 B2
(45) Date of Patent: Aug. 18, 2026

(54) DUAL-SCREEN VISUAL AID DISPLAY METHOD AND APPARATUS FOR PEOPLE WITH LOW VISION, AND DEVICE

(71) Applicant: HANGZHOU DUKANG TECHNOLOGY CO., LTD., Hangzhou (CN)

(72) Inventors: Zezhi Gong, Hangzhou (CN); Xiang Ying, Hangzhou (CN); Xinwei Huang, Hangzhou (CN)

(73) Assignee: HANGZHOU DUKANG TECHNOLOGY CO., LTD., Hangzhou (CN)

( * ) Notice: Subject to any disclaimer, the term of this patent is extended or adjusted under 35 U.S.C. 154(b) by 194 days.

(21) Appl. No.: 18/798,931

(22) Filed: Aug. 9, 2024

(65) Prior Publication Data

US 2025/0336030 A1 Oct. 30, 2025

(30) Foreign Application Priority Data

Apr. 29, 2024 (CN) ......................... 202410525591.8

(51) Int. Cl.

| | |
|---|---|
| ***G06T 3/40*** | (2024.01) |
| ***G06F 3/14*** | (2006.01) |
| ***G06T 11/10*** | (2026.01) |
| ***G16H 30/40*** | (2018.01) |

(52) U.S. Cl.

CPC .................. *G06T 3/40* (2013.01); *G06F 3/14* (2013.01); *G06F 3/1446* (2013.01); *G06T 11/10* (2026.01); *G16H 30/40* (2018.01); *G06F 2203/04805* (2013.01); *G06F 2203/04806* (2013.01)

(58) Field of Classification Search

CPC ............. G06F 3/14; G06F 2203/04806; G06F 2203/04805; G06T 3/40

See application file for complete search history.

(56) References Cited

U.S. PATENT DOCUMENTS

2022/0083208 A1* 3/2022 Kutas .................. G06F 3/04845
2024/0211034 A1* 6/2024 Ye ........................... G06F 3/013

* cited by examiner

*Primary Examiner* — Matthew Salvucci
(74) *Attorney, Agent, or Firm* — NZ Carr Law Office

(57) ABSTRACT

The present disclosure provides a dual-screen visual aid display method and apparatus for people with low vision, and a device. The method includes: determining, on a main screen based on a current microscopic control zoom level selected by a user, position information of a microscopic area virtual frame with a display image as a reference; mapping, according to display parameters of the main screen and a resolution of a current display image on the main screen, the position information of the microscopic area virtual frame to position information of a microscopic highlight frame in a main screen coordinate system; scanning a moving state of the microscopic highlight frame under the main screen coordinate system to obtain starting point coordinates of the moved microscopic highlight frame; reversely mapping the starting point coordinates of the moved microscopic highlight frame to obtain starting point coordinates of the moved microscopic area virtual frame; and extracting, based on the width and height of the microscopic area virtual frame and the starting point coordinates of the moved microscopic area virtual frame, image content in the microscopic area virtual frame, and performing microscopic zooming, on a secondary screen, on the image content.

19 Claims, 5 Drawing Sheets

DUAL-SCREEN VISUAL AID DISPLAY METHOD AND APPARATUS FOR PEOPLE WITH LOW VISION, AND DEVICE

CROSS-REFERENCE TO RELATED APPLICATIONS

The present application claims the priority of the Chinese patent application with an application No. 20/241,0525591.8 on Apr. 29, 2024. The abstract, description, claims, and drawings of the description of the present application are used in its entirety by the present application.

BACKGROUND OF THE INVENTION

Field of the Invention

The present disclosure relates to the technical field of auxiliary display, in particular to a dual-screen visual aid display method and apparatus for people with low vision, and a device.

Description of the Related Art

An electronic visual aid is a visual aid product mainly provided for the visually impaired, and the main components thereof are a camera, a processor and a display screen. An image is acquired by the camera and processed, and then is subjected to zoom in, color change or other adjustments on the display screen, so that people with low vision (for example, people with low vision caused by presbyopia and eye diseases) can see target content on the display screen more clearly.

Traditional electronic visual aids are mostly of a structure with a single display screen, but with the continuous technological development of visual aids, there are also dual-screen visual aid structures on the market. In an existing dual-screen visual aid, two display screens usually show different scenes, for example, one display screen is used for close views, while the other display screen is used for distant views; or both display screens are used for synchronous replication display. However, whether the display screens are used for synchronous close views or distant views or for synchronous replication display, the maximum field of view of each display image only has a size of a display region of a single display screen, and images in each display screen may only zoom in or out as a whole. That is, an existing dual-screen visual aid may neither expand the field of view, nor realize global preview and local zoom view at the same time, is simplex in function, and thus cannot meet user requirements.

BRIEF SUMMARY OF THE INVENTION

In order to overcome the defects in the prior art, the present disclosure provides a dual-screen visual aid method and apparatus for people with low vision, and a device.

In order to achieve the above purposes, the present disclosure provides a dual-screen visual aid display method for people with low vision. The method includes:

determining, on a main screen based on a current microscopic control zoom level zoomLevel selected by a user, position information of a microscopic area virtual frame with a display image as a reference, the position information including starting point coordinates ($Zoom_x$, $Zoom_y$) and a width and height ($Zoom_w$, $Zoom_h$) of the microscopic area virtual frame;

mapping, according to display parameters of the main screen and a resolution $W_0*H_0$ of a current display image on the main screen, the position information of the microscopic area virtual frame to position information of a microscopic highlight frame in a main screen coordinate system, the position information of the microscopic highlight frame including starting point coordinates ($OSD_x$, $OSD_y$) and a width and height ($OSD_w$, $OSD_h$) of the microscopic highlight frame;

scanning a moving state of the microscopic highlight frame under the main screen coordinate system to obtain starting point coordinates ($OSD_x'$, $OSD_y'$) of the moved microscopic highlight frame;

reversely mapping the starting point coordinates ($OSD_x'$, $OSD_y'$) of the moved microscopic highlight frame to obtain starting point coordinates ($Zoom_x'$, $Zoom_y'$) of the moved microscopic area virtual frame;

extracting, based on the width and height ($Zoom_w$, $Zoom_h$) of the microscopic area virtual frame and the starting point coordinates ($Zoom_x'$, $Zoom_y'$) of the moved microscopic area virtual frame, image content in the microscopic area virtual frame; and performing microscopic zooming, on a secondary screen, on the extracted image content in the microscopic area virtual frame.

According to one embodiment of the present disclosure, the display parameters of the main screen include: starting point coordinates ($X_o$, $Y_o$) of a global visual area window and a width and height ($DW_o$, $DH_o$) of the global visual area window when all image information and contours are displayed on the main screen; and the position information of the microscopic area virtual frame is mapped to the position information of the microscopic highlight frame in the main screen coordinate system by the following formulas:

$$OSD_w = \mathrm{Zoom}_w * DW_o/W_o;$$

$$OSD_h = \mathrm{Zoom}_h * DH_o/H_o;$$

$$OSD_x = X_o + \mathrm{Zoom}_x * DW_o/W_o; \text{ and}$$

$$OSD_y = Y_o + \mathrm{Zoom}_y * DH_o/H_o,$$

where $W_o$ denotes a width of the display image, and $H_o$ denotes a height of the display image.

According to one embodiment of the present disclosure, a size of the main screen is 16:9, and a resolution of the main screen is $D_w*D_h$; and based on a change of the current microscopic control zoom level zoomLevel selected by the user, the display image is subjected to zooming in by a two-stage zoom strategy: in the case where the microscopic control zoom level zoomLevel is from 0 to $ZoomLevel_{16R9}$, the display image is subjected to zooming in by adopting a first zoom strategy to adapt to the size of the main screen, $ZoomLevel_{16R9}$ being a microscopic control zoom level when the display image first adapts to the display size of the main screen; and in the case where the microscopic control zoom level zoomLevel is from $ZoomLevel_{16R9}$ to $ZoomLevel_{max}$, the display image adapting to the size of the main screen is subjected to zooming in in equal proportion by adopting a second zoom strategy.

According to one embodiment of the present disclosure, the first zoom strategy is:

when $(W_o*D_h \geq H_o*D_w)$ is met, the position information of the microscopic area virtual frame is as follows:

$$Zoom_w = W_o - 2*32*ZoomLevel;$$

$$Zoom_h = H_o;$$

$$Zoom_x = Zoom_{x0} - 32;$$

$$Zoom_y = Zoom_{y0};$$

when $(W_o*D_h < H_o*D_w)$ is met, the position information of the microscopic area virtual frame is as follows:

$$Zoom_w = W_o;$$

$$Zoom_h = H_o - 2*32*ZoomLevel;$$

$$Zoom_x = Zoom_{x0};$$

$$Zoom_y = Zoom_{y0} - 32;$$

the second zoom strategy is:

after stepping of each microscopic control zoom level with zoomLevel+1, the position information of the microscopic area virtual frame is calculated as follows:

$$Zoom_w = Zoom_{w0} - 32*2;$$

$$Zoom_h = Zoom_{h0} - 32*2;$$

$$Zoom_x = Zoom_{x0} - 32; \text{ and}$$

$$Zoom_y = Zoom_{y0} - 32,$$

where $(Zoom_{x0}, Zoom_{y0})$ and $(Zoom_{w0}, Zoom_{h0})$ denote the starting point coordinates and the width and height of the microscopic area virtual frame before the change of the microscopic control zoom level zoomLevel respectively, and $(Zoom_x, Zoom_y)$ and $(Zoom_w, Zoom_h)$ denote the starting point coordinates and the width and height of the microscopic area virtual frame determined based on the current microscopic control zoom level zoomLevel.

According to one embodiment of the present disclosure, the adjustment range of the current microscopic control zoom level zoomLevel is between 0 and $ZoomLevel_{max}$, and a maximum microscopic control zoom level $ZoomLevel_{max}$ is related to the resolution of the display image and the resolution the main screen.

According to one embodiment of the present disclosure, when the moving state of the microscopic highlight frame is scanned under the main screen coordinate system, it is determined whether the starting point coordinates and end point coordinates of the microscopic highlight frame exceed the global visual area window when all the image information and contours are displayed on the main screen; if yes, the starting point coordinates or end point coordinates of the microscopic highlight frame are embedded into boundary coordinates of the global visual area window to form the position information of the moved microscopic highlight frame.

According to one embodiment of the present disclosure, after the image content in the microscopic area virtual frame is extracted, the image content is subjected to color change based on a background color selected by the user, and then subjected to microscopic zooming on the secondary screen.

According to one embodiment of the present disclosure, the dual-screen visual aid display method for people with low vision further includes an extended display mode, and the mode includes:

determining, according to the current microscopic control zoom level zoomLevel selected by the user, position information of a main screen field magnification area on the display image, and determining, with boundaries of the main screen field magnification area as a reference, position information of a secondary screen field magnification area contiguously adjacent to the main screen field magnification area in a horizontal or vertical direction of the display image, the position information including starting point coordinates and a width and height of the field magnification area;

scanning a state change of the current microscopic control zoom level zoomLevel and a moving state of the main screen field magnification area, and when either of the two changes, recalculating the position information of the main screen field magnification area and synchronously updating the position information of the secondary screen field magnification area; and acquiring image information of the main screen field magnification area and image information of the secondary screen field magnification area, and separately zooming in and displaying the image information in a main screen display area and a secondary screen display area to achieve extended display.

According to one embodiment of the present disclosure, the dual-screen visual aid display method for people with low vision further includes a synchronous replication mode, and the mode includes:

determining, according to the current microscopic control zoom level zoomLevel selected by the user, position information of a main screen field magnification area on the display image, the position information including starting point coordinates and a width and height of the field magnification area;

scanning a state change of the current microscopic control zoom level zoomLevel and a moving state of the main screen field magnification area, and when either of the two changes, recalculating the position information of the main screen field magnification area; and acquiring image information in the main screen field magnification area, and displaying same in a main screen display area and a secondary screen display area to achieve synchronous replication display.

In another aspect, the present disclosure further provides a dual-screen visual aid display apparatus for people with low vision. The apparatus includes a position information determining unit, a position information mapping unit, a state scanning and updating unit, a position information reverse mapping unit, a content extraction unit, and a display control unit. The position information determining unit is configured to determine, on a main screen based on a current microscopic control zoom level zoomLevel selected by a user, position information of a microscopic area virtual frame with a display image as a reference, the position information including starting point coordinates $(Zoom_x, Zoom_y)$ and a width and height $(Zoom_w, Zoom_h)$ of the microscopic area virtual frame. The position information mapping unit is configured to map, according to display parameters of the main screen and a resolution $W_0*H_0$ of a current display image on the main screen, the position information of the microscopic area virtual frame to position information of a microscopic highlight frame in a main screen coordinate system, the position information of the microscopic highlight frame including starting point coordinates ($OSD_x$, $OSD_y$) and a width and height ($OSD_w$,$OSD_h$) of the microscopic highlight frame. The state scanning and updating unit is configured to scan a moving state of the microscopic highlight frame under the main screen coordinate system to obtain starting point coordinates ($OSD_x'$, $OSD_y'$) of the moved microscopic highlight frame. The position information reverse mapping unit is configured to reversely map the starting point coordinates ($OSD_x'$, $OSD_y'$) of the moved microscopic highlight frame to obtain starting point coordinates ($Zoom_x'$, $Zoom_y'$) of the moved microscopic area virtual frame. The content extraction unit is configured to extract, based on the width and height ($Zoom_w$, $Zoom_h$) of the microscopic area virtual frame and the starting point coordinates ($Zoom_x'$, $Zoom_y'$) of the moved microscopic area virtual frame, image content in the microscopic area virtual frame. The display control unit is configured to perform microscopic zooming, on a secondary screen, on the extracted image content in the microscopic area virtual frame.

According to one embodiment of the present disclosure, the apparatus has an extended display mode. In the mode, the position information determining unit determines, according to the current microscopic control zoom level zoomLevel selected by the user, position information of a main screen field magnification area on the display image, and determines, with boundaries of the main screen field magnification area as a reference, position information of a secondary screen field magnification area contiguously adjacent to the main screen field magnification area in a horizontal or vertical direction of the display image, the position information including starting point coordinates and a width and height of the field magnification area; the state scanning and updating unit scans a state change of the current microscopic control zoom level zoomLevel and a moving state of the main screen field magnification area and when either of the two changes, recalculates the position information of the main screen field magnification area and synchronously updates the position information of the secondary screen field magnification area; and the content extraction unit acquires an image in the main screen field magnification area and an image in the secondary screen field magnification area respectively, and the display control unit separately zooms in the two acquired images and displays same in a main screen display area and a secondary screen display area to achieve extended display.

According to one embodiment of the present disclosure, the apparatus has a synchronous replication mode. In the mode, the position information determining unit determines, according to the current microscopic control zoom level zoomLevel selected by the user, position information of a main screen field magnification area on the display image, the position information including starting point coordinates and a width and height of the field magnification area; the state scanning and updating unit scans a state change of the current microscopic control zoom level zoomLevel and a moving state of the main screen field magnification area and when either of the two changes, recalculates the position information of the main screen field magnification area; and the content extraction unit acquires images in the main screen field magnification area, and the display control unit displays the acquired images in the main screen display area and the secondary screen display area to achieve synchronous replication display.

In another aspect, the present disclosure further provides a computer device. The computer device includes a memory and a processor, the memory having a computer program stored therein, and the processor, when executing the computer program, implementing the steps in the above dual-screen visual aid method for people with low vision.

In summary, in the dual-screen visual aid display method for people with low vision, the position information of the microscopic area virtual frame with the display image as a reference is determined on the main screen according to the current microscopic control zoom level zoomLevel selected by the user, and the content of the display image in the microscopic area virtual frame is extracted and subjected to microscopic zooming on the secondary screen. Thus, the full image preview display on the main screen and local zoom into view on the secondary screen are realized. When the microscopic area virtual frame is moved to change the microscopic zoom content, the present disclosure, based on the mapping relationship between the position information of the microscopic area virtual frame and the microscopic highlight frame, transforms the scanning of the position information of the microscopic area virtual frame, which is affected by image parameters and difficult to scan and locate, into the scanning of the position information of the microscopic highlight frame under the standard main screen coordinate system. The method does not need to locate the microscopic zoom content on the display image, but locates the microscopic highlighted area on the main screen display area. After the position information of the moved microscopic highlight area is determined, reverse mapping is performed to obtain the position information of the microscopic area virtual frame. Finally, the microscopic zoom content is extracted from the mapped microscopic area virtual frame and displayed on the secondary screen. This microscopic zoom method not only realizes global preview and local zoom, but also greatly reduces the difficulty of microscopic zoom positioning, and greatly improves the response speed of microscopic zoom of the secondary screen.

Further, the dual-screen visual aid display method for people with low vision according to the present disclosure also provides the dual-screen extended display mode and the dual-screen synchronous replication mode. In the dual-screen extended display mode, the secondary screen displays an image under the other field of view that is continuously connected to the display image of the main screen in the vertical direction or horizontal direction, which extends the scope of image content that may be read at large multiples, and the field of view in the vertical or horizontal direction is expanded twice compared with the dual-screen synchronous replication mode for higher reading connectivity.

In order to make the above and other objectives, features and advantages of the present disclosure more clearly understood, preferred embodiments are given and described in detail below in conjunction with the accompanying drawings.

DETAILED DESCRIPTION OF THE INVENTION

Figure 1:
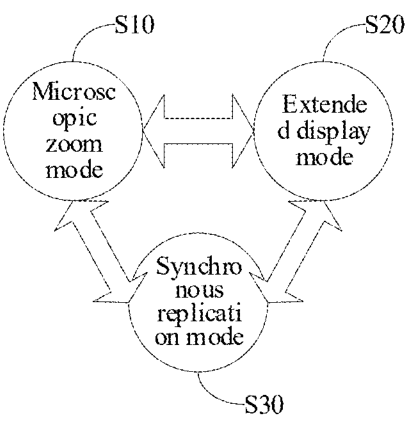
FIG. 1 is a schematic diagram of multi-display model switching of a dual-screen visual aid display method for people with low vision according to an embodiment of the present disclosure.

As shown in FIG. 1, a dual-screen visual aid display method for people with low vision according to this embodiment has three display modules, namely a microscopic zoom mode S10, an extended display mode S20, and a synchronous replication mode S30. Users may switch the three modes according to needs. However, the present disclosure does not limit this in any way. In other embodiments, the dual-screen visual aid display method for people with low vision may have only the microscopic zoom mode S10, or combine the microscopic zoom mode S10 with either the extended display mode S20 or the synchronous replication mode S30; or, extend the existing dual-screen display functions such as synchronous close views or distant views (achieved by means of dual cameras) on the basis of the microscopic zoom mode S10.

As shown in FIG. 1, the dual-screen visual aid display method for people with low vision according to this embodiment includes, in the microscopic zoom mode S10, the following steps:

Step S101, determine, on a main screen based on a current microscopic control zoom level zoomLevel selected by a user, position information of a microscopic area virtual frame with a display image as a reference, the position information including starting point coordinates ($Zoom_x$, $Zoom_y$) and a width and height ($Zoom_w$, $Zoom_h$) of the microscopic area virtual frame.

Step S102: Map, according to display parameters of the main screen and a resolution $W_0*H_0$ of a current display image on the main screen, the position information of the microscopic area virtual frame to position information of a microscopic highlight frame in a main screen coordinate system, the position information of the microscopic highlight frame including starting point coordinates ($OSD_x$, $OSD_y$) and a width and height ($OSD_w$, $OSD_h$) of the microscopic highlight frame.

Step S103: Scan a moving state of the microscopic highlight frame under the main screen coordinate system to obtain starting point coordinates ($OSD_x'$, $OSD_y'$) of the moved microscopic highlight frame.

Step S104: Reversely map the starting point coordinates ($OSD_x'$, $OSD_y'$) of the moved microscopic highlight frame to obtain starting point coordinates ($Zoom_x'$, $Zoom_y'$) of the moved microscopic area virtual frame.

Step S105: Extract, based on the width and height ($Zoom_w$, $Zoom_h$) of the microscopic area virtual frame and the starting point coordinates ($Zoom_x'$, $Zoom_y'$) of the moved microscopic area virtual frame, image content in the microscopic area virtual frame.

Step S106: Perform microscopic zooming, on a secondary screen, on the extracted image content in the microscopic area virtual frame.

In this embodiment, the starting point coordinates of the microscopic area virtual frame refer to the coordinates of the upper left corner of the microscopic area virtual frame, and ($Zoom_x+Zoom_w$, $Zoom_y+Zoom_h$) denotes end point coordinates of the microscopic area virtual frame. Correspondingly, the starting point coordinates ($OSD_x$, $OSD_y$) of the microscopic highlight frame are the coordinates of the upper left corner of the microscopic highlight frame, and ($OSD_x+OSD_w$, $OSD_y$30 $OSD_h$) denotes end point coordinates of the microscopic highlight frame. However, the present disclosure does not limit this in any way. In other embodiments, the coordinates of the lower left corner of the microscopic area virtual frame may also be defined as the starting point coordinates.

The dual-screen visual aid display method for people with low vision according to this embodiment will be described in detail below in combination with FIG. 1 to FIG. 3.

Figure 2:
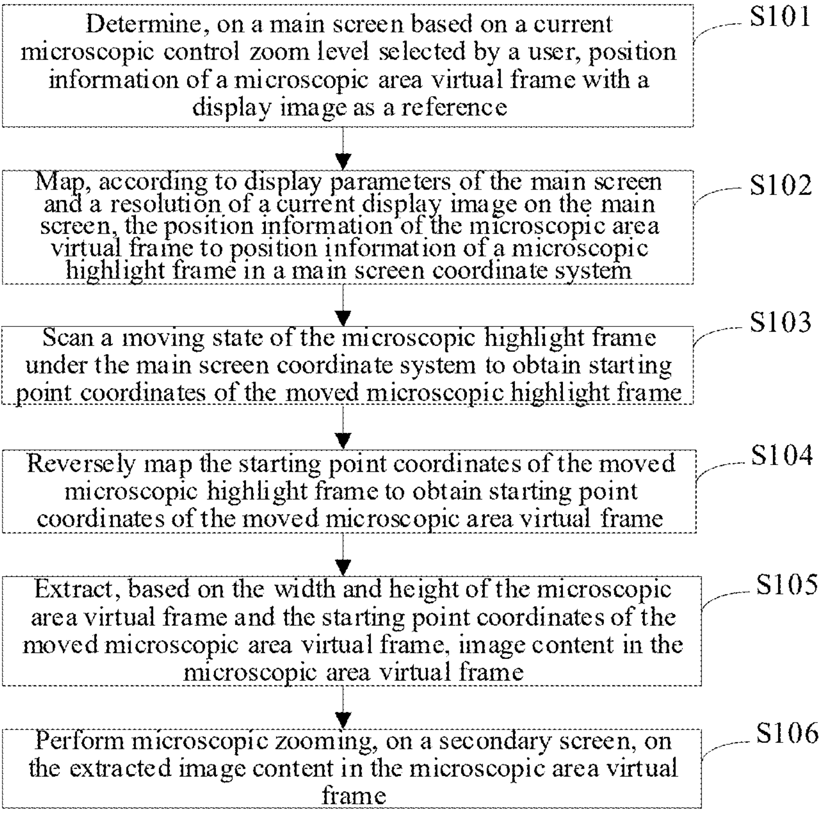
FIG. 2 is a schematic flow diagram of a microscopic zoom mode in FIG. 1.
Figure 3:
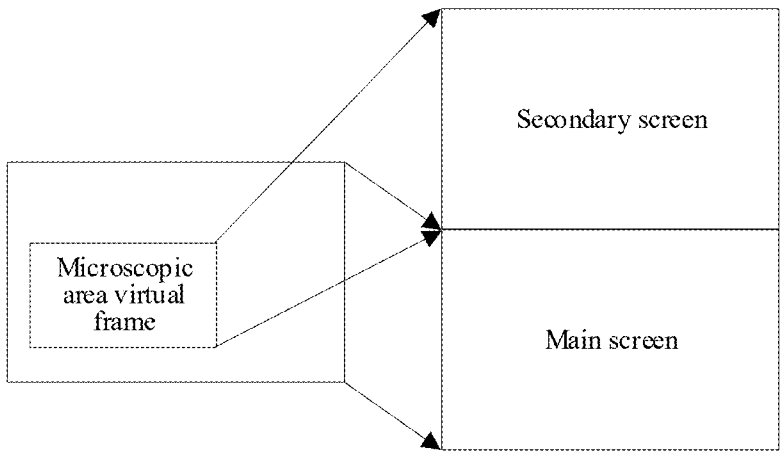
FIG. 3 is a schematic diagram of a microscopic zoom mode in FIG. 1.

As shown in FIG. 2, the microscopic zoom mode S10 begins with step S101: determine the position of the microscopic area virtual frame on the display image based on the current microscopic control zoom level zoomLevel selected by the user. The current microscopic control zoom level zoomLevel is a parameter for the user to adjust the size of the display image on the main screen by pressing buttons, touching the main screen or gesture sensing without touching the main screen. Specifically, this step includes: step S1011, a visual coordinate area, with a resolution of $D_w*D_h$, of the display image $W_o*H_o$ on the main screen. In the microscopic zoom mode, it needs to be ensured that all image information and contours are displayed on the main screen to achieve global preview. This embodiment defines the starting point coordinates of the global visual area window on the main screen as ($X_o$, $Y_o$) and the width and height of the global visual area window as ($DW_o$, $DH_o$). When ($W_o*D_h>H_o*D_w$) is met, the starting point coordinates and the width and height of the global visual area window are calibrated as follows:

$$DW_o = D_w;$$

$$DH_o = (H_o * D_w / W_o)\&0xFFFE;\text{ and}$$

$$X_o = ((D_w - DW_o) >> 1)\&0xFFFE.$$

$$Y_o = ((D_H - DH_o) >> 1)\&0xFFFE;$$

Otherwise, the same are calculated and calibrated by the following formulas:

$$DW_o = (W_o * D_h / H_o)\&0xFFFE;$$

$$DH_o = D_h;$$

$$X_o = ((D_w - DW_o) >> 1)\&0xFFFE;\text{ and}$$

$$Y_o = ((D_H - DH_o) >> 1)\&0xFFFE,$$

where &0xFFFE denotes conversion to binary. $D_w*D_h$ denotes the resolution of the main screen, which refers to the number of pixels per inch displayed on the main screen. W0*H0 denotes the resolution of the display image, which refers to the amount of information stored in the display image, and indicates how many pixels per inch of the image.

Step S1012, after the starting point coordinates and the width and height of the global visual area window on the main screen are determined, initial coordinates and an initial width and height of the microscopic area virtual frame when initially entering the microscopic zoom mode are determined. Specifically, $ZoomLevel_0$ is defined as an initial microscopic control zoom level, $ZoomLevel_0=Zoomlevel_{max}/2$ is set when entering the microscopic zoom mode, and $ZoomLevel_{max}$ is the maximum microscopic control zoom level supported by the microscopic zoom mode. However, the present disclosure does not limit this in any way. In other embodiments, $ZoomLevel_0$ is also selected as other proportional parameters of $Zoomlevel_{max}$, such as ⅓, ¼, or ⅕. Based on the determined $ZoomLevel_0$, if $(W_o*D_h \geq H_o*D_w)$, the width and height ($Zoom_{wo}'$, $Zoom_{ho}'$) of the microscopic area virtual frame when initially entering the microscopic zoom mode are determined by the following formulas:

$$Zoom'_{w0} = W_o - 2*32*ZoomLevel_0; \text{ and}$$

$$Zoom'_{h0} = H_o.$$

On the contrary, the width and height ($Zoom_{wo}'$, $Zoom_{ho}'$) of the microscopic area virtual frame when initially entering the microscopic zoom mode are acquired by the following formulas:

$$Zoom'_{w0} = W_o.$$

$$Zoom'_{h0} = H_o - 2*32*ZoomLevel_0;$$

The mapping coordinates ($x_o$, $y_o$) of the starting point coordinates ($X_o$, $Y_o$) of the global visual area window on the main screen under the virtual coordinate system with an image as a reference are used as the initial coordinates of the microscopic area virtual frame when initially entering the microscopic zoom mode; and the coordinates ($X_o$, $Y_o$) and ($x_o$, $y_o$) may be obtained by performing mapping based on the reverse mapping relationship of step S103. That is, in the initial state, the coordinates ($Zoom_{x0}'$, $Zoom_{y0}'$) of the microscopic area virtual frame are the coordinates ($x_o$, $y_o$). However, the present disclosure does not limit this in any way. In other embodiments, the mapping coordinates of the center position of the global visual area window on the main screen under the virtual coordinate system with an image as a reference may also be used as the initial coordinates of the microscopic area virtual frame when initially entering the microscopic zoom mode.

Step S1013, a zoom strategy of the microscopic area virtual frame in the microscopic zoom mode is determined to obtain the position information of the microscopic area virtual frame after the current microscopic control zoom level ZoomLevel is adjusted. The adjustment range of the current microscopic control zoom level zoomLevel is between 0 and $ZoomLevel_{max}$, and the maximum microscopic control zoom level $ZoomLevel_{max}$ is related to the resolution of the display image and the resolution the main screen. In this embodiment, in order to make display images of different sizes adapt to the global visual area window in the main screen, the display images are zoomed in using a two-stage zoom strategy based on the current microscopic control zoom level selected by the user. Specifically, the display size of the main screen is selected as 16:9, and a first zoom strategy is used to zoom in the display image when the microscopic control zoom level zoomLevel changes between 0 and $ZoomLevel_{16R9}$, $ZoomLevel_{16R9}$ being the microscopic control zoom level when the display image first adapts to the display size of the main screen. When the microscopic control zoom level zoomLevel changes between $ZoomLevel_{16R9}$ and $ZoomLevel_{max}$, a second zoom strategy is used to zoom in the display image adapting to the size of the main screen in equal proportion.

Although this embodiment illustrates the display size of the main screen of 16:9 as an example, the present disclosure does not limit this in any way. In other embodiments, other sizes of the main screen may be used; in this case, the display image may also be zoomed in for display by using a zoom strategy of two or three or more stages. The two-stage zoom strategy provided in this embodiment will be described in detail below.

In this step, the microscopic control zoom level $ZoomLevel_{16R9}$ when the display image first adapts to the display size (e.g. 16:9) of the main screen in the microscopic zoom mode and the maximum microscopic control zoom level $ZoomLevel_{max}$ supported by the microscopic zoom mode are first determined. Specifically, when $(W_o*D_h \geq H_o*D_w)$ is met, $$ZoomLevel_{16R9} = (W_o - H_o*D_w/D_h)/32/2; \text{ and}$$

$$ZoomLevel_{max} = ZoomLevel_{16R9} + (H_o - 192)/18/2.$$

Otherwise, $$ZoomLevel_{16R9} = (H_o - W_o*D_h/D_w)/32/2; \text{ and}$$

$$ZoomLevel_{max} = ZoomLevel_{16R9} + (W_o - 192)/36/2.$$

The current microscopic control zoom level zoomLevel is then determined, and when zoomLevel is between 0 and $ZoomLevel_{16R9}$, the first zoom strategy is:

when $(W_o*D_h \geq H_o*D_w)$ is met, a horizontal stepping strategy is adopted, and the position information of the microscopic area virtual frame is adjusted based on the following formulas:

$$Zoom_w = W_o - 2*32*ZoomLevel;$$

$$Zoom_h = H_o;$$

$$Zoom_x = Zoom_{x0} - 32;$$

$$Zoom_y = Zoom_{y0}.$$

When $(W_o*D_h < H_o*D_w)$ is met, the position information of the microscopic area virtual frame is as follows:

$$Zoom_w = W_o;$$

$$Zoom_h = H_o - 2*32*ZoomLevel;$$

-continued $$Zoom_x = Zoom_{x0}; \text{ and}$$

$$Zoom_y = Zoom_{y0} - 32.$$

When zoomLevel is between $ZoomLevel_{16R9}$ and $ZoomLevel_{max}$, the second zoom strategy is adopted: after stepping of each microscopic control zoom level with zoomLevel+1, the position information of the microscopic area virtual frame is calculated as follows:

$$Zoom_w = Zoom_{w0} - 32*2;$$

$$Zoom_h = Zoom_{h0} - 32*2;$$

$$Zoom_x = Zoom_{x0} - 32; \text{ and}$$

$$Zoom_y = Zoom_{y0} - 32,$$

where $(Zoom_{x0}, Zoom_{y0})$ and $(Zoom_{w0}, Zoom_{h0})$ denote the starting point coordinates and the width and height of the microscopic area virtual frame of the previous zoomLevel respectively, and $(Zoom_x, Zoom_y)$ denotes the starting point coordinates of the microscopic area virtual frame determined based on the current microscopic control zoom level zoomLevel. When initially entering the microscopic zoom mode, $Zoom_{x0}=Zoom_{x0}'$; $Zoom_{y0}=Zoom_{y0}'$; $Zoom_{w0}=Zoom_{w0}'$; and $Zoom_{h0}=Zoom_{h0}'$.

After the position information of the microscopic area virtual frame is determined based on the microscopic area scaling strategy in step S101, step S102 is performed: the position information of the microscopic highlight frame corresponding to the microscopic area virtual frame on the main screen with the resolution of $D_w*D_h$ at each zoom level is determined, the position information of the microscopic highlight frame including starting point coordinates $(OSD_x, OSD_y)$ and the width and height $(OSD_w, OSD_h)$ of the microscopic highlight frame. Specifically, according to the display parameters of the main screen and the resolution W0*H0 of the current display image on the main screen, the position information of the microscopic area virtual frame is mapped to the position information of the microscopic highlight frame by adopting the following mapping relationship:

$$OSD_w = Zoom_w * DW_o / W_o;$$

$$OSD_h = Zoom_h * DH_o / H_o;$$

$$OSD_x = X_o + Zoom_x * DW_o / W_o; \text{ and}$$

$$OSD_y = Y_o + Zoom_y * DH_o / H_o,$$

where the display parameters of the main screen include the starting point coordinates $(X_o, Y_o)$ of the global visual area window and the width and height $(DW_o, DH_o)$ of the global visual area window when all image information and contours are displayed on the main screen, $W_o$ denotes the width of the display image, and Ho denotes the height of the display image.

After the position information of the microscopic highlight frame under the main screen coordinate system is determined in step S102, step S103 is performed: a moving state of the microscopic highlight frame by the user under the main screen coordinate system is scanned to obtain starting point coordinates $(OSD_x', OSD_y')$ of the moved microscopic highlight frame. In this embodiment, the position information of the microscopic area virtual frame with the display image as a reference is mapped to the position information of the microscopic highlight frame with the main screen coordinate system as a reference, and scanning of the change of the position state of the microscopic area virtual frame may be achieved by scanning the position state of the microscopic highlight frame. The main screen coordinate system is a standard rectangular coordinate system related only to the display parameters of the main screen, which is unrelated to the state (such as the tilt and clarity of an image) of the display image, which not only greatly reduces the difficulty of microscopic positioning, but also greatly improves the speed and accuracy of positioning, and greatly increases the response speed of microscopic zoom of the secondary screen. Existing cursor positioning functions, such as SetConsoleCursorPosition in windows, may be used to locate the starting point coordinates of the microscopic highlight frame under the main screen.

Specifically, when the moving state of the microscopic highlight frame is scanned under the main screen coordinate system, it is determined whether the starting point coordinates and the end point coordinates of the microscopic highlight frame exceed the global visual area window when all the image information and contours are displayed on the main screen; if yes, the starting point coordinates or end point coordinates of the microscopic highlight frame are embedded into boundary coordinates of the global visual area window to form the position information of the moved microscopic highlight frame. Specifically, if it is determined that the starting point coordinates $(OSD_x', OSD_y')$ of the microscopic highlight frame have exceeded the left boundary coordinate $X_o$ of the global visual area window, the left boundary coordinate $X_o$ of the global visual area window is used as the horizontal coordinate of the microscopic highlight frame for correction, and the corrected starting point coordinates of the microscopic highlight frame are $(X_o, OSD_y')$. Similarly, if it is determined that the end point coordinates $(OSD_x'+OSD_w, OSD_y'+OSD_h)$ of the microscopic highlight frame have exceeded the right boundary coordinate $X_o+DW_o$, and the upper boundary of the global visual area window, the corrected starting point coordinates $(OSD_x', OSD_y')$ of the microscopic highlight frame are $(X_o+DW_o, Y_o)$. If it is determined that the end point coordinates $(OSD_x'+OSD_w, OSD_y'+OSD_h)$ of the microscopic highlight frame have exceeded the right boundary coordinate $X_o+DW_o$ and the low boundary coordinate $Y_o+DH_o$ of the global visual area window, the corrected starting point coordinates $(OSD_x', OSD_y')$ of the microscopic highlight frame are $(X_o+DW_o, Y_o+DH_o)$. By means of the boundary correction of the microscopic highlight frame based on the boundary coordinates of the global visual area window, the secondary screen may accurately display the image content in the microscopic area virtual frame. Specifically, the user may move the microscopic highlight frame by pressing buttons, touching the sensitive main screen or performing gesture sensing without touching the screen or the like.

After the starting point coordinates $(OSD_x', OSD_y')$ of the moved microscopic highlight frame are obtained in step S103, step S104 is performed: the starting point coordinates $(OSD_x', OSD_y')$ of the moved microscopic highlight frame are reversely mapped to the starting point coordinates $(Zoom_x', Zoom_y')$ of the microscopic area virtual frame. Specifically, mapping is performed by adopting the following reverse mapping relationship:

$$\text{Zoom}'_x = \left((OSD'_x - X_o) * W_o / DW_o\right) \& 0xFFFC.$$

$$\text{Zoom}'_y = \left((OSD'_y - Y_o) * \frac{W_o}{DW_o}\right) \& 0xFFFC;$$

On this basis, combined with the width and height ($\text{Zoom}_w$, $\text{Zoom}_h$) of the microscopic area virtual frame in the current microscopic control zoom level zoomLevel calculated in step S101, the position information of the moved microscopic area virtual frame is obtained and the image content in the microscopic area virtual frame is extracted (step S105).

After the image content in the microscopic area virtual frame is obtained in step S105, the content is sent to the secondary screen and subjected to microscopic zooming on the secondary screen (step S106). Specifically, during microscopic zooming on the secondary screen, it is necessary to determine the starting point coordinates ($\text{DISP}_x$, $\text{DISP}_y$) and the width and height ($\text{DISP}_w$, $\text{DISP}_h$) of the microscopic zoom area on the secondary screen with the resolution of $D_w' * D_h'$.

When ($\text{Zoom}_w * D_h \geq \text{Zoom}_h * D_w$) is met, the coordinate calculation formulas are:

$$DISP_w = D'_w;$$

$$DISP_h = \left(\text{Zoom}_w * D'_w / \text{Zoom}_h\right) \& 0xFFFE;$$

$$DISP_x = ((D'_w - DISP_w) >> 1) \& 0xFFFE; \text{ and}$$

$$DISP_y = ((D'_h - DISP_h) \gg 1) \& 0xFFF.$$

On the contrary, the calculation formulas are as follows:

$$DISP_w = \left(\text{Zoom}_w * D'_h / \text{Zoom}_h\right) \& 0xFFFE;$$

$$DISP_h = D'_h;$$

$$DISP_x = ((D'_w - DISP_w) \gg 1) \& 0xFFFE; \text{ and}$$

$$DISP_y = ((D'_w - DISP_h) >> 1) \& 0xFFFE.$$

After the starting point coordinates ($\text{DISP}_x$, $\text{DISP}_y$) and the width and height ($\text{DISP}_w$, $\text{DISP}_h$) of the microscopic zoom area are determined on the secondary screen, the image content in the microscopic area virtual frame obtained in S105 is zoomed in in equal proportions for display on the secondary screen, so that the global preview of the main screen and the local microscopic zoom of the secondary screen are achieved, which provides two different display fields of view for users with low vision to have a better experience. Further, the image content may also be subjected to color change based on the background color selected by the user and then subjected to microscopic zooming on the secondary screen, which is more conducive to the reading of low-vision people affected by color, for example, people with red-green color blindness.

Figure 4:
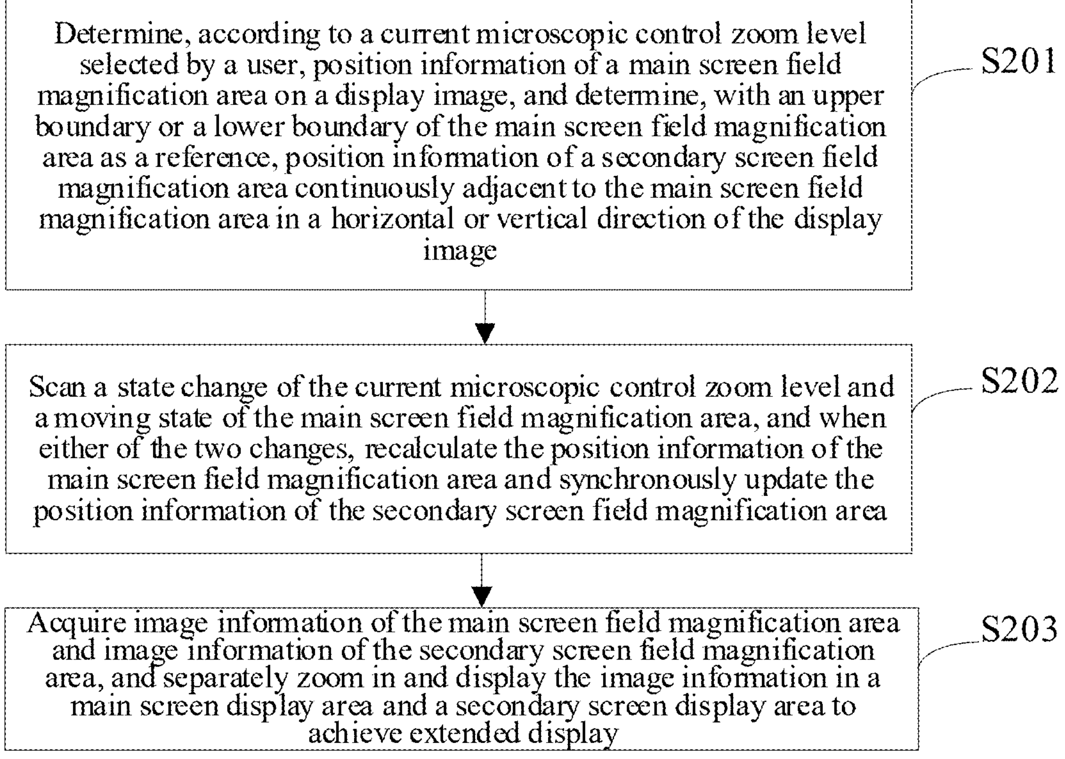
FIG. 4 is a schematic flow diagram of an extended display mode in FIG. 1.
Figure 5:
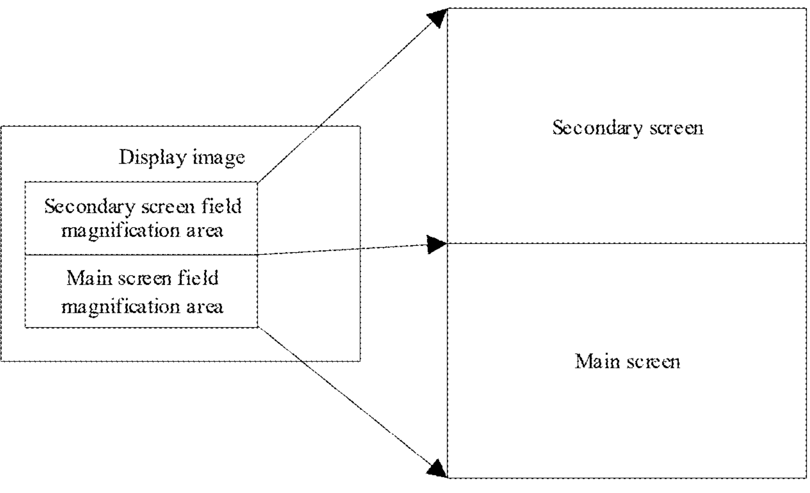
FIG. 5 is a schematic diagram of an extended display mode in FIG. 4.

Further, the dual-screen visual aid display method for people with low vision according to this embodiment includes the extended display mode S20. As shown in FIG. 4. the mode includes:

Step S201, according to the current microscopic control zoom level zoomLevel selected by the user, position information of a main screen field magnification area is determined on the display image, and with boundaries of the main screen field magnification area as a reference, position information of a secondary screen field magnification area contiguously adjacent to the main screen field magnification area is determined in a horizontal or vertical direction of the display image, the position information including starting point coordinates and a width and height of the field magnification area. Specifically, as shown in FIG. 5, the position information of the secondary screen field magnification area may be determined in the vertical direction of the main screen field magnification area based on the upper or lower boundary of the main screen field magnification area; alternatively, the position information of the secondary screen field magnification area may be determined in the horizontal direction of the main screen field magnification area based on the left or right boundary of the main screen field magnification area. The dual-screen visual aid display apparatus for people with low vision according to the present disclosure may store the microscopic control zoom level zoomLevel, including storing zoomLevel the user familiar with or zoomLevel at the last operation. Based on the memory pf zoomLevel, when the user enters the extended display mode, zoomLevel of the previous mode (such as the microscopic zoom mode or the synchronous replication mode) is used as the initial microscopic control zoom level of the extended display mode. At the same time, the position information of the main screen field magnification area may inherit the position information of the microscopic area virtual frame in the microscopic zoom mode or the position information of the main screen field magnification area in the synchronous replication mode. However, the present disclosure does not limit this in any way.

Step S202, a state change of the current microscopic control zoom level zoomLevel and a moving state of the main screen field magnification area are scanned, and when either of the two changes, the position information of the main screen field magnification area is recalculated, and the position information of the secondary screen field magnification area is synchronously updated. Specifically, the moving state of the main screen field magnification area is determined by scanning the change of the starting point coordinates of the main screen field magnification area with the display image as a reference. For the state change of the microscopic control zoom level zoomLevel, the width and height of the main screen field magnification area may be adjusted according to the preset zoom strategy. For example, for the main screen with the display size of 16:9, the width and height ($\text{DispH}_w$, $\text{DispH}_h$) of the main screen field magnification area after stepping of each zoom level with zoomLevel+1 is calculated using the following strategies:

$$DispH_w = DispH_{w0} - 32 * 2; \text{ and}$$

$$DispH_h = DispH_{h0} - 32 * 2,$$

where ($\text{DispH}_{w0}$, $\text{DispH}_{h0}$) denotes the width and height of the main screen field magnification area at the previous microscopic control zoom level. The position of the display image at the upper boundary of the main screen field magnification area is determined based on the starting point coordinates and the width and height of the main screen field magnification area. The starting point coordinates of the secondary screen field magnification area are obtained based on the position, and the width and height of the secondary screen field magnification area are the same as those of the main screen.

Accordingly, the position information of the moved secondary screen field magnification area is obtained.

Step S203, image information of the main screen field magnification area and image information of the secondary screen field magnification area are acquired, and are subjected to separated zooming in for display in a main screen display area and a secondary screen display area to achieve extended display. Similarly, in order to be more conducive to the reading of people with low vision affected by color, such as the reading of patients with red and green color blindness, the image information in the main screen field magnification area and the secondary screen field magnification area may also be subjected to color change based on the background color selected by the user, and then displayed on the main screen and the secondary screen respectively.

Figure 6:
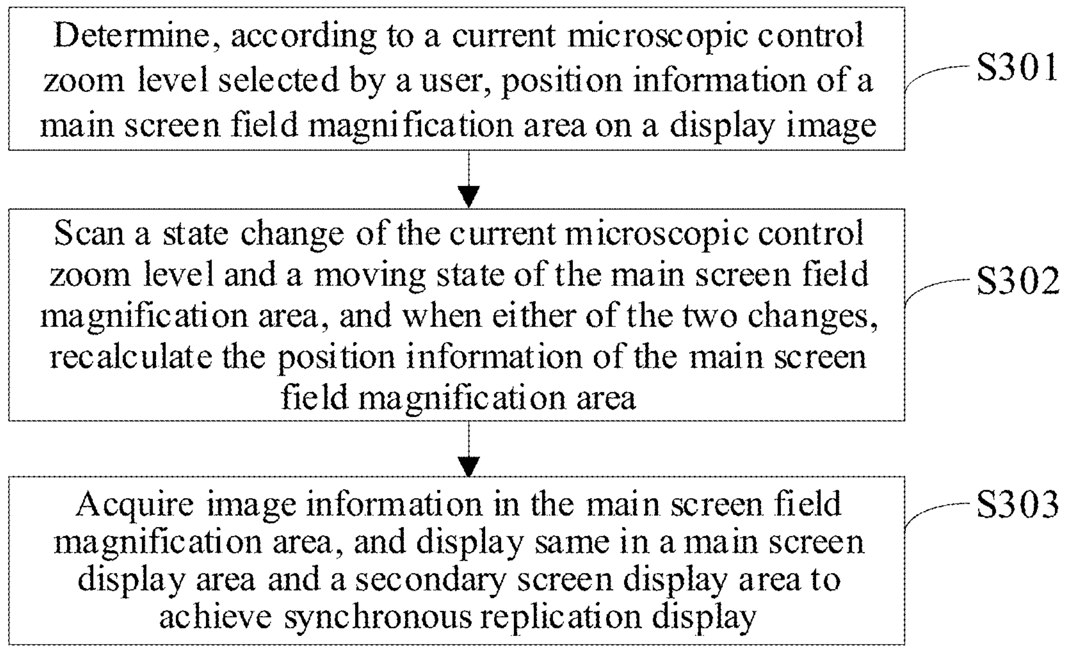
FIG. 6 is a schematic flow diagram of a synchronous replication mode in FIG. 1.

Specifically, in the extended display mode S20, if the main screen displays a display image with a magnification factor of 30 times, the secondary screen displays up-down continuous display image content also with a magnification factor of 30 times, and the specific effect is shown in FIG. 5. This display mode has the advantage of increasing the scope of the image content that the user may read at large multiples, and the field of view in the vertical direction is expanded by two times compared to the synchronous replication mode S30 at the same magnification factor, which makes reading have higher connectivity, especially for the reading of vertical text. Further, the dual-screen visual aid display method for people with low vision according to this embodiment also includes the synchronous replication mode S30. As shown in FIG. 6, the mode includes:

Step S301: according to the current microscopic control zoom level zoomLevel selected by the user, the position information of the main screen field magnification area is determined on the display image, the position information including the starting point coordinates and the width and height of the field magnification area. Specifically, the dual-screen visual aid display apparatus for people with low vision according to the present disclosure may store the microscopic control zoom level zoomLevel, including storing zoomLevel the user familiar with or zoomLevel at the last operation. Based on the memory of zoomLevel, when the user enters the synchronous replication mode, zoomLevel of the previous mode (such as the microscopic zoom mode or the extended display mode) is used as the initial microscopic control zoom level of the synchronous replication mode. At the same time, the position information of the main screen field magnification area may inherit the position information of the microscopic area virtual frame in the microscopic zoom mode or the position information of the main screen field magnification area in the extended display mode. However, the present disclosure does not limit this in any way.

Step S302: a state change of the current microscopic control zoom level zoomLevel and a moving state of the main screen field magnification area are scanned, and when either of the two changes, the position information of the main screen field magnification area is recalculated.

Figure 7:
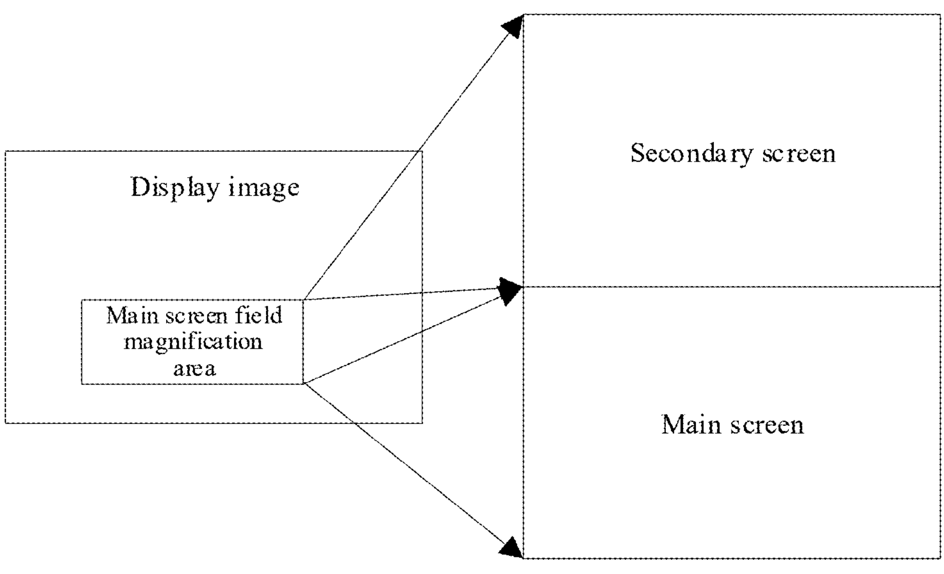
FIG. 7 is a schematic diagram of a synchronous replication mode in FIG. 6.

Step S303: image information in the main screen field magnification area is acquired, and displayed in a main screen display area and a secondary screen display area to achieve synchronous replication display, as shown in FIG. 7.

The dual-screen visual aid display method for people with low vision according to this embodiment may be arbitrarily switched between the microscopic zoom mode S10, the extended display mode S20 and the synchronous replication mode S30, providing people with low vision with multiple display modes based on dual screens.

The main screen and the secondary screen provided in this embodiment may be two independent screens integrated on the same device, or two display areas of the same screen in the same device; or may be two separate screens arranged on different devices.

Correspondingly, this embodiment provides a dual-screen visual aid display apparatus for people with low vision. The apparatus includes a position information determining unit 10, a position information mapping unit 20, a state scanning and updating unit 30, a position information reverse mapping unit 40, a content extraction unit 50, and a display control unit 60. The position information determining unit 10 is configured to determine, on a main screen based on a current microscopic control zoom level zoomLevel selected by a user, position information of a microscopic area virtual frame with a display image as a reference, the position information including starting point coordinates ($Zoom_x$, $Zoom_y$) and a width and height ($Zoom_w$, $Zoom_h$) of the microscopic area virtual frame. The position information mapping unit 20 is configured to map, according to display parameters of the main screen and a resolution $W_0*H_0$ of a current display image on the main screen, the position information of the microscopic area virtual frame to position information of a microscopic highlight frame in a main screen coordinate system, the position information of the microscopic highlight frame including starting point coordinates ($OSD_x$, $OSD_y$) and a width and height ($OSD_w$,$OSD_h$) of the microscopic highlight frame. The state scanning and updating unit 30 is configured to scan a moving state of the microscopic highlight frame under the main screen coordinate system to obtain starting point coordinates ($OSD_x'$, $OSD_y'$) of the moved microscopic highlight frame. The position information reverse mapping unit 40 is configured to reversely map the starting point coordinates ($OSD_x'$, $OSD_y'$) of the moved microscopic highlight frame to obtain starting point coordinates ($Zoom_x'$, $Zoom_y'$) of the moved microscopic area virtual frame. The content extraction unit 50 is configured to extract, based on the width and height ($Zoom_w$, $Zoom_h$) of the microscopic area virtual frame and the starting point coordinates ($Zoom_x'$, $Zoom_y'$) of the moved microscopic area virtual frame, image content in the microscopic area virtual frame. The display control unit 60 is configured to perform microscopic zooming, on a secondary screen, on the extracted image content in the microscopic area virtual frame.

According to one embodiment of the present disclosure, the apparatus has an extended display mode. In the mode, the position information determining unit 10 determines, according to the current microscopic control zoom level zoomLevel selected by the user, position information of a main screen field magnification area on the display image, and determines, with boundaries of the main screen field magnification area as a reference, position information of a secondary screen field magnification area contiguously adjacent to the main screen field magnification area in a horizontal or vertical direction of the display image, the position information including starting point coordinates and a width and height of the field magnification area; the state scanning and updating unit 30 scans a state change of the current microscopic control zoom level zoomLevel and a moving state of the main screen field magnification area and when either of the two changes, recalculates the position information of the main screen field magnification area and synchronously updates the position information of the secondary screen field magnification area; and the content extraction unit 50 acquires an image in the main screen field magnification area and an image in the secondary screen field magnification area, and the display control unit 60 separately zooms in the two acquired images and displays same in a main screen display area and a secondary screen display area respectively to achieve extended display.

According to one embodiment of the present disclosure, the apparatus has a synchronous replication mode. In the mode, the position information determining unit 10 determines, according to the current microscopic control zoom level zoomLevel selected by the user, the position information of a main screen field magnification area on the display image, position information including starting point coordinates and a width and height of the field magnification area; the state scanning and updating unit 30 scans a state change of the current microscopic control zoom level zoomLevel and a moving state of the main screen field magnification area and when either of the two changes, recalculates the position information of the main screen field magnification area; and the content extraction unit 50 acquires images in the main screen field magnification area, and the display control unit 60 displays the acquired images in the main screen display area and the secondary screen display area to achieve synchronous replication display.

The specific limits of the dual-screen visual aid display apparatus for people with low vision may refer to the above limits of the dual-screen visual aid display method for people with low vision, which will not be repeated here. Each module of the above-mentioned dual-screen visual aid display apparatus for people with low vision may be realized in whole or in part by software, hardware and combinations thereof. The above modules may be embedded in the hardware form or independent of a processor in a computer device, and may also be stored in the software form in a memory of the computer device, so that the processor may call and perform the corresponding operations of the above modules.

Figure 9:
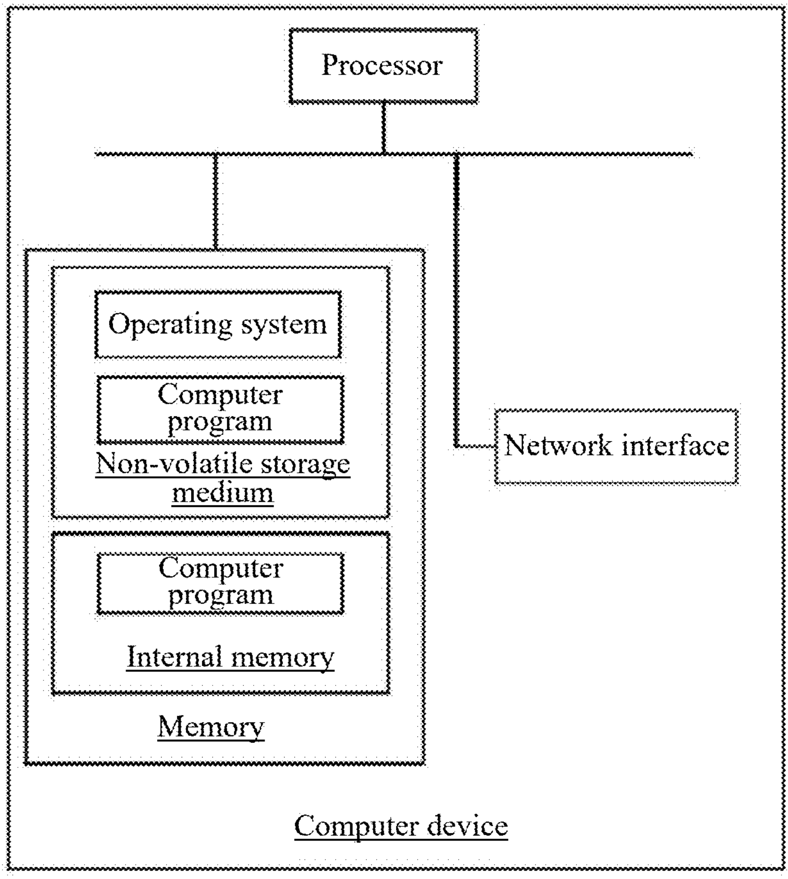
FIG. 9 is a schematic structural diagram of a computer device according to an embodiment of the present disclosure.

FIG. 9 is a diagram of an internal structure of a computer device according to one embodiment. The computer device includes a processor, a memory and a network interface connected through a system bus. The memory includes a non-volatile storage medium and an internal memory. The non-volatile storage medium of the computer device stores an operating system and a computer program. When the computer program is executed by the processor, the processor can realize a lightweight face attribute recognition model training method. A computer program can also be stored in the internal memory, and when the computer program is executed by the processor, the processor can perform the lightweight face attribute recognition model training method.

It may be understood by those skilled in the art that the structure shown in FIG. 9 is only a block diagram of a part of the structure related to this application scheme and does not constitute a limitation of the computer device to which this application scheme is applied. Specifically, the computer device may include more or less components than shown in the figure, or combine certain components, or have different component arrangements.

Figure 8:
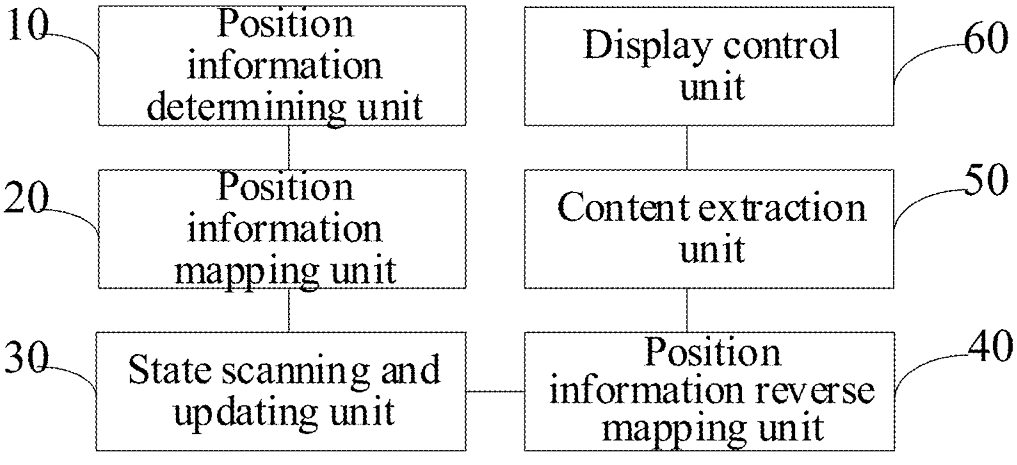
FIG. 8 is a schematic structural diagram of a dual-screen visual aid display apparatus for people with low vision according to an embodiment of the present disclosure.

In one embodiment, the dual-screen visual aid display apparatus for people with low vision provided in the present application may be realized in the form of a computer program that can be run on the computer device shown in FIG. 9. The memory of the computer device may store the program modules that form the dual-screen visual aid display apparatus for people with low vision, for example, the position information determining unit 10, the position information mapping unit 20, the state scanning and updating unit 30, the position information reverse mapping unit 40, and the display control unit 50 as shown in FIG. 8. The computer program formed by each program module enables the processor to perform the steps in the dual-screen visual aid display method for people with low vision according to the embodiments of the present application as described in this specification.

In summary, in the dual-screen visual aid display method for people with low vision, the position information of the microscopic area virtual frame with the display image as a reference is determined on the main screen according to the current microscopic control zoom level zoomLevel selected by the user, and the content of the display image in the microscopic area virtual frame is extracted and subjected to microscopic zooming on the secondary screen. Thus, the full image preview display on the main screen and local zoom into view on the secondary screen are realized. When the microscopic area virtual frame is moved to change the microscopic zoom content, the present disclosure, based on the mapping relationship between the position information of the microscopic area virtual frame and the microscopic highlight frame, transforms the scanning of the position information of the microscopic area virtual frame, which is affected by image parameters and difficult to scan and locate, into the scanning of the position information of the microscopic highlight frame under the standard main screen coordinate system. The method does not need to locate the microscopic zoom content on the display image, but locates the microscopic highlighted area on the main screen display area. After the position information of the moved microscopic highlight area is determined, reverse mapping is performed to obtain the position information of the microscopic area virtual frame. Finally, the microscopic zoom content is extracted from the mapped microscopic area virtual frame and displayed on the secondary screen. This microscopic zoom method not only realizes global preview and local zoom, but also greatly reduces the difficulty of microscopic zoom positioning, and greatly improves the response speed of microscopic zoom of the secondary screen.

Further, the dual-screen visual aid display method for people with low vision according to the present disclosure also provides the dual-screen extended display mode and the dual-screen synchronous replication mode. In the dual-screen extended display mode, the secondary screen displays an image under the other field of view that is continuously connected to the display image of the main screen in the vertical direction or horizontal direction, which extends the scope of image content that may be read at large multiples, and the field of view in the vertical or horizontal direction is expanded twice compared with the dual-screen synchronous replication mode for higher reading connectivity.

Although the present invention has been described with reference to the above preferred embodiments, the present invention is not limited thereto. Any person skilled in the art may make slight changes and embellishments without departing from the spirit and scope of the present invention, so that the scope of protection of the present invention shall be subject to the scope of protection required by the claims.

The invention claimed is:

1. A dual-screen visual aid display method for people with low vision, comprising:

determining, on a main screen based on a current microscopic control zoom level zoomLevel selected by a user, position information of a microscopic area virtual frame with a display image as a reference, the position information comprising starting point coordinates ($Zoom_x$, $Zoom_y$) and a width and height ($Zoom_w$, $Zoom_h$) of the microscopic area virtual frame;

mapping, according to display parameters of the main screen and a resolution $W_0*H_0$ of a current display image on the main screen, the position information of the microscopic area virtual frame to position information of a microscopic highlight frame in a main screen coordinate system, the position information of the microscopic highlight frame comprising starting point coordinates ($OSD_x$, $OSD_y$) and a width and height ($OSD_w$,$OSD_h$) of the microscopic highlight frame;

scanning a moving state of the microscopic highlight frame under the main screen coordinate system to obtain starting point coordinates ($OSD_w'$, $OSD_y'$) of the moved microscopic highlight frame;

reversely mapping the starting point coordinates ($OSD_x'$, $OSD_y'$) of the moved microscopic highlight frame to obtain starting point coordinates ($Zoom_x'$, $Zoom_y'$) of the moved microscopic area virtual frame;

extracting, based on the width and height ($Zoom_w$, $Zoom_h$) of the microscopic area virtual frame and the starting point coordinates ($Zoom_x'$, $Zoom_y'$) of the moved microscopic area virtual frame, image content in the microscopic area virtual frame; and performing microscopic zooming, on a secondary screen, on the extracted image content in the microscopic area virtual frame.

2. The dual-screen visual aid display method for people with low vision according to claim 1, wherein the display parameters of the main screen comprise: starting point coordinates ($X_o$, $Y_o$) of a global visual area window and a width and height ($DW_o$, $DH_o$) of the global visual area window when all image information and contours are displayed on the main screen; and the position information of the microscopic area virtual frame is mapped to the position information of the microscopic highlight frame in the main screen coordinate system by the following formulas:

$$OSD_w = Zoom_w * DW_o / W_o;$$

$$OSD_h = Zoom_h * DH_o / H_o;$$

$$OSD_x = X_o + Zoom_x * DW_o / W_o; \text{ and}$$

$$OSD_y = Y_o + Zoom_y * DH_o / H_o,$$

wherein $W_o$ denotes a width of the display image, and $H_o$ denotes a height of the display image.

3. The dual-screen visual aid display method for people with low vision according to claim 1, wherein a size of the main screen is 16:9, and a resolution of the main screen is $D_w*D_h$; and based on a change of the current microscopic control zoom level zoomLevel selected by the user, the display image is subjected to zooming in by a two-stage zoom strategy: in the case where the microscopic control zoom level zoomLevel is from 0 to $ZoomLevel_{16R9}$, the display image is subjected to zooming in by adopting a first zoom strategy to adapt to the size of the main screen, $ZoomLevel_{16R9}$ being a microscopic control zoom level when the display image first adapts to the display size of the main screen; and in the case where the microscopic control zoom level zoomLevel is from $ZoomLevel_{16R9}$ to $ZoomLevel_{max}$, the display image adapting to the size of the main screen is subjected to zooming in in equal proportion by adopting a second zoom strategy.

4. The dual-screen visual aid display method for people with low vision according to claim 3, wherein the first zoom strategy is:

when $W_o*D_h \geq H_o*D_w$ is met, the position information of the microscopic area virtual frame is as follows:

$$Zoom_w = W_o - 2*32*ZoomLevel;$$

$$Zoom_h = H_o;$$

$$Zoom_x = Zoom_{x0} - 32;$$

$$Zoom_y = Zoom_{y0};$$

when $Zoom_x = Zoom_{xo}$–is met, the position information of the microscopic area virtual frame is as follows:

$$Zoom_w = W_o;$$

$$Zoom_h = H_o - 2*32*ZoomLevel;$$

$$Zoom_x = Zoom_{x0};$$

$$Zoom_y = Zoom_{y0} - 32;$$

the second zoom strategy is:

after stepping of each microscopic control zoom level with zoomLevel+1, the position information of the microscopic area virtual frame is calculated as follows:

$$Zoom_w = Zoom_{w0} - 32*2;$$

$$Zoom_h = Zoom_{h0} - 32*2;$$

$$Zoom_x = Zoom_{x0} - 32; \text{ and}$$

$$Zoom_y = Zoom_{y0} - 32,$$

wherein ($Zoom_{x0}$, $Zoom_{y0}$) and ($Zoom_{w0}$, $Zoom_{h0}$) denote the starting point coordinates and the width and height of the microscopic area virtual frame before the change of the microscopic control zoom level zoomLevel respectively, and ($Zoom_x$, $Zoom_y$) and ($Zoom_w$, $Zoom_h$) denote the starting point coordinates and the width and height of the microscopic area virtual frame determined based on the current microscopic control zoom level zoomLevel.

5. The dual-screen visual aid display method for people with low vision according to claim 3, wherein the adjustment range of the current microscopic control zoom level zoomLevel is between 0 and $ZoomLevel_{max}$, and a maximum microscopic control zoom level $ZoomLevel_{max}$ is related to the resolution of the display image and the resolution of the main screen.

6. The dual-screen visual aid display method for people with low vision according to claim 1, wherein when the moving state of the microscopic highlight frame is scanned under the main screen coordinate system, it is determined whether the starting point coordinates and end point coordinates of the microscopic highlight frame exceed the global visual area window when all the image information and contours are displayed on the main screen; if yes, the starting point coordinates or end point coordinates of the microscopic highlight frame are embedded into boundary coordinates of the global visual area window to form the position information of the moved microscopic highlight frame.

7. The dual-screen visual aid display method for people with low vision according to claim 1, wherein after the image content in the microscopic area virtual frame is extracted, the image content is subjected to color change based on a background color selected by the user, and then subjected to microscopic zooming on the secondary screen.

8. The dual-screen visual aid display method for people with low vision according to claim 1, further comprising an extended display mode, and the mode comprising:

determining, according to the current microscopic control zoom level zoomLevel selected by the user, position information of a main screen field magnification area on the display image, and determining, with boundaries of the main screen field magnification area as a reference, position information of a secondary screen field magnification area contiguously adjacent to the main screen field magnification area in a horizontal or vertical direction of the display image, the position information comprising starting point coordinates and a width and height of the field magnification area;

scanning a state change of the current microscopic control zoom level zoomLevel and a moving state of the main screen field magnification area, and when either of the two changes, recalculating the position information of the main screen field magnification area and synchronously updating the position information of the secondary screen field magnification area; and acquiring image information of the main screen field magnification area and image information of the secondary screen field magnification area, and separately zooming in and displaying the image information in a main screen display area and a secondary screen display area to achieve extended display.

9. The dual-screen visual aid display method for people with low vision according to claim 8, wherein when the microscopic zoom mode is switched to the extended display mode, zoomLevel in the microscopic zoom mode before switching is used as an initial microscopic control zoom level of the extended display mode, and the position information of the microscopic area virtual frame in the microscopic zoom mode before switching is used as the position information of the main screen field magnification area.

10. The dual-screen visual aid display method for people with low vision according to claim 1, further comprising a synchronous replication mode, and the mode comprising:

determining, according to the current microscopic control zoom level zoomLevel selected by the user, position information of a main screen field magnification area on the display image, the position information comprising starting point coordinates and a width and height of the field magnification area;

scanning a state change of the current microscopic control zoom level zoomLevel and a moving state of the main screen field magnification area, and when either of the two changes, recalculating the position information of the main screen field magnification area; and acquiring image information in the main screen field magnification area, and displaying same in a main screen display area and a secondary screen display area to achieve synchronous replication display.

11. A dual-screen visual aid display apparatus for people with low vision, comprising:

a position information determining unit, configured to determine, on a main screen based on a current microscopic control zoom level zoomLevel selected by a user, position information of a microscopic area virtual frame with a display image as a reference, the position information comprising starting point coordinates ($Zoom_x$, $Zoom_y$) and a width and height ($Zoom_w$, $Zoom_h$) of the microscopic area virtual frame;

a position information mapping unit, configured to map, according to display parameters of the main screen and a resolution $W_0*H_0$ of a current display image on the main screen, the position information of the microscopic area virtual frame to position information of a microscopic highlight frame in a main screen coordinate system, the position information of the microscopic highlight frame comprising starting point coordinates ($OSD_x$, $OSD_y$) and a width and height ($OSD_w$, $OSD_h$) of the microscopic highlight frame;

a state scanning and updating unit, configured to scan a moving state of the microscopic highlight frame under the main screen coordinate system to obtain starting point coordinates ($OSD_x'$, $OSD_y'$) of the moved microscopic highlight frame;

a position information reverse mapping unit, configured to reversely map the starting point coordinates ($OSD_x'$, $OSD_y'$) of the moved microscopic highlight frame to obtain starting point coordinates ($Zoom_x'$, $Zoom_y'$) of the moved microscopic area virtual frame;

a content extraction unit, configured to extract, based on the width and height ($Zoom_w$, $Zoom_h$) of the microscopic area virtual frame and the starting point coordinates ($Zoom_x'$, $Zoom_y'$) of the moved microscopic area virtual frame, image content in the microscopic area virtual frame; and a display control unit, configured to perform microscopic zooming, on a secondary screen, on the extracted image content in the microscopic area virtual frame.

12. The dual-screen visual aid display apparatus for people with low vision according to claim 11, wherein the display parameters of the main screen comprise: starting point coordinates ($X_o$, $Y_o$) of a global visual area window and a width and height ($DW_o$, $DH_o$) of the global visual area window when all image information and contours are displayed on the main screen; and the position information of the microscopic area virtual frame is mapped to the position information of the microscopic highlight frame in the main screen coordinate system by the following formulas:

$$OSD_w = \mathrm{Zoom}_w * DW_o / W_o;$$

$$OSD_h = \mathrm{Zoom}_h * DH_o / H_o;$$

$$OSD_x = X_o + \mathrm{Zoom}_x * DW_o / W_o; \text{ and}$$

$$OSD_y = Y_o + \mathrm{Zoom}_y * DH_o / H_o,$$

wherein $W_o$ denotes a width of the display image, and $H_o$ denotes a height of the display image.

13. The dual-screen visual aid display apparatus for people with low vision according to claim 11, wherein a size of the main screen is 16:9, and a resolution of the main screen is $D_w*D_h$;

based on a change of the current microscopic control zoom level zoomLevel selected by the user, the display image is subjected to zooming in by a two-stage zoom strategy: in the case where the microscopic control zoom level zoomLevel is from 0 to $ZoomLevel_{16R9}$, the display image is subjected to zooming in by adopting a first zoom strategy to adapt to the size of the main screen, $ZoomLevel_{16R9}$ being a microscopic control zoom level when the display image first adapts to the display size of the main screen; and in the case where the microscopic control zoom level zoomLevel is from $ZoomLevel_{16R9}$ to $ZoomLevel_{max}$, the display image adapting to the size of the main screen is subjected to zooming in in equal proportion by adopting a second zoom strategy.

14. The dual-screen visual aid display apparatus for people with low vision according to claim 13, wherein the first zoom strategy is:

when $W_o{*}D_h \geq H_o{*}D_w$ is met, the position information of the microscopic area virtual frame is as follows:

$$Zoom_w = W_o - 2*32*ZoomLevel;$$

$$Zoom_h = H_o;$$

$$Zoom_x = Zoom_{x0} - 32;$$

$$Zoom_y = Zoom_{y0};$$

when $W_o{*}D_h < H_o{*}D_w$ is met, the position information of the microscopic area virtual frame is as follows:

$$Zoom_w = W_o;$$

$$Zoom_h = H_o - 2*32*ZoomLevel;$$

$$Zoom_x = Zoom_{x0};$$

$$Zoom_y = Zoom_{y0} - 32;$$

the second zoom strategy is:

after stepping of each microscopic control zoom level with zoomLevel+1, the position information of the microscopic area virtual frame is calculated as follows:

$$Zoom_w = Zoom_{w0} - 32*2;$$

$$Zoom_h = Zoom_{h0} - 32*2;$$

$$Zoom_x = Zoom_{x0} - 32; \text{ and}$$

$$Zoom_y = Zoom_{y0} - 32,$$

wherein $(Zoom_{x0}, Zoom_{y0})$ and $(Zoom_{w0}, Zoom_{h0})$ denote the starting point coordinates and the width and height of the microscopic area virtual frame before the change of the microscopic control zoom level zoomLevel respectively, and $(Zoom_x, Zoom_y)$ and $(Zoom_w, Zoom_h)$ denote the starting point coordinates and the width and height of the microscopic area virtual frame determined based on the current microscopic control zoom level zoomLevel.

15. The dual-screen visual aid display apparatus for people with low vision according to claim 13, wherein the adjustment range of the current microscopic control zoom level zoomLevel is between 0 and $ZoomLevel_{max}$, and a maximum microscopic control zoom level $ZoomLevel_{max}$ is related to the resolution of the display image and the resolution of the main screen.

16. The dual-screen visual aid display apparatus for people with low vision according to claim 11, wherein when the moving state of the microscopic highlight frame is scanned under the main screen coordinate system, it is determined whether the starting point coordinates and end point coordinates of the microscopic highlight frame exceed the global visual area window when all the image information and contours are displayed on the main screen; if yes, the starting point coordinates or end point coordinates of the microscopic highlight frame are embedded into boundary coordinates of the global visual area window to form the position information of the moved microscopic highlight frame.

17. The dual-screen visual aid display apparatus for people with low vision according to claim 11, wherein after the image content in the microscopic area virtual frame is extracted, the image content is subjected to color change based on a background color selected by the user, and then subjected to microscopic zooming on the secondary screen.

18. The dual-screen visual aid display apparatus for people with low vision according to claim 11, wherein the apparatus has an extended display mode, and in the mode, the position information determining unit determines, according to the current microscopic control zoom level zoomLevel selected by the user, position information of a main screen field magnification area on the display image, and determines, with boundaries of the main screen field magnification area as a reference, position information of a secondary screen field magnification area contiguously adjacent to the main screen field magnification area in a horizontal or vertical direction of the display image, the position information comprising starting point coordinates and a width and height of the field magnification area;

the state scanning and updating unit scans a state change of the current microscopic control zoom level zoomLevel and a moving state of the main screen field magnification area, and when either of the two changes, recalculates the position information of the main screen field magnification area and synchronously updates the position information of the secondary screen field magnification area; and the content extraction unit acquires an image in the main screen field magnification area and an image in the secondary screen field magnification area respectively, and the display control unit separately zooms in the two acquired images and displays same in a main screen display area and a secondary screen display area to achieve extended display.

19. The dual-screen visual aid display apparatus for people with low vision according to claim 11, wherein the apparatus has a synchronous replication mode, and in the mode, the position information determining unit determines, according to the current microscopic control zoom level zoomLevel selected by the user, position information of a main screen field magnification area on the display image, the position information comprising starting point coordinates and a width and height of the field magnification area;

the state scanning and updating unit scans a state change of the current microscopic control zoom level zoomLevel and a moving state of the main screen field magnification area, and when either of the two changes, recalculates the position information of the main screen field magnification area; and the content extraction unit acquires images in the main screen field magnification area, and the display control unit displays the acquired images in the main screen display area and the secondary screen display area to achieve synchronous replication display.

* * * * *